United States Patent [19]

Ploog et al.

[11] Patent Number: 4,865,614

[45] Date of Patent: Sep. 12, 1989

[54] QUATERNARY 2-ALKYLIMIDAZOLINIUM SALTS AS FABRIC SOFTENERS

[75] Inventors: Uwe Ploog, Haan; Guenter Uphues, Monheim, both of Fed. Rep. of Germany

[73] Assignee: Henkel Kommanditgesellschaft auf Aktien, Duesseldorf, Fed. Rep. of Germany

[21] Appl. No.: 57,555

[22] Filed: Jun. 3, 1987

[30] Foreign Application Priority Data

Jun. 5, 1986 [DE] Fed. Rep. of Germany ....... 3618944

[51] Int. Cl.$^4$ .................. D06M 13/46; C07D 233/14
[52] U.S. Cl. .......................... 8/115.6; 8/189; 252/8.8; 548/353; 548/354
[58] Field of Search ................. 548/354, 353; 8/189, 8/115.6; 252/8.8

[56] References Cited

U.S. PATENT DOCUMENTS

| | | | |
|---|---|---|---|
| 3,591,405 | 7/1971 | McCarty et al. | 427/158 |
| 3,636,114 | 1/1972 | Tobler et al. | 564/292 |
| 3,932,495 | 1/1976 | Martinsson et al. | 564/294 |
| 3,972,855 | 8/1976 | Martinsson et al. | 558/38 |
| 3,976,581 | 8/1976 | Rose | 564/147 X |
| 4,104,175 | 8/1978 | Martinsson et al. | 252/8.57 |
| 4,127,489 | 11/1978 | Pracht et al. | 252/8.8 |
| 4,212,983 | 7/1980 | Phillips et al. | 548/352 |
| 4,399,044 | 8/1983 | Richmond | 548/354 X |
| 4,458,080 | 7/1984 | Boehmke et al. | 548/354 |
| 4,526,694 | 7/1985 | Puchta et al. | 252/8.8 |

FOREIGN PATENT DOCUMENTS

| | | |
|---|---|---|
| 0004334 | 11/1983 | Australia . |
| 0013780 | 8/1980 | European Pat. Off. . |
| 0056695 | 7/1982 | European Pat. Off. . |
| 0075170 | 3/1983 | European Pat. Off. . |
| 1619043 | 10/1969 | Fed. Rep. of Germany . |
| 2930849 | 2/1981 | Fed. Rep. of Germany . |
| 6808958 | 12/1969 | Netherlands . |
| 0639444 | 11/1983 | Switzerland . |
| 2167092 | 5/1986 | United Kingdom . |

OTHER PUBLICATIONS

Chemical Abstracts 95:8758k (1981), [Eur. Pat. Appl. 23,335, Ploog et al., 2/4/81].
S. Billenstein et al., *J. Am. Oil Chem. Soc.*, 61 (1984), pp. 353–357.

Primary Examiner—Richard A. Schwartz
Attorney, Agent, or Firm—Ernest G. Szoke; Wayne C. Jaeschke; Real J. Grandmaison

[57] ABSTRACT

The reaction of 2-alkylimidazolines with ethylene oxide or propylene oxide gives quaternary 2-alkyl-2-imidazolinium salts corresponding to the following general formula

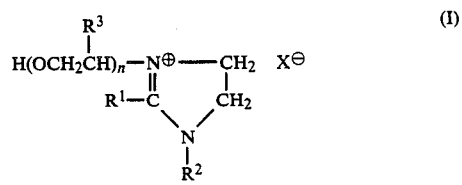

wherein
$R^1$ represents a straight-chain or branched-chain substituted or unsubstituted alkyl or alkenyl radical containing from 7 to 21 carbon atoms,
$R^2$ represents one of the following radicals

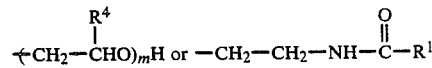

$R^3$ represents hydrogen or methyl,
$R^4$ represents hydrogen or methyl,
$X^\ominus$ represents the anion of a non-oxidizing and non-corrosive inorganic acid or of an organic mono- or polycarboxylic acid,
n statistically represents a whole or fraction number of from 1 to 20, and
m represents an integer of from 1 to 3, which may be used for softening laundered fabrics.

10 Claims, No Drawings

QUATERNARY 2-ALKYLIMIDAZOLINIUM SALTS AS FABRIC SOFTENERS

BACKGROUND OF THE INVENTION

1. Field of the Invention

This invention relates to quaternary 2-alkylimidazolinium salts, to a process for their production and to their use.

2. Discussion of Related Art

It has long been known that quaternary tetraalkylammonium compounds containing two long-chain alkyl radicals and two short-chain alkyl radicals, for example, two $C_{16}$–$C_{18}$ alkyl radicals and two methyl radicals, impart a soft feel to washed fabrics when added to the final rinse of a washing process. These fabric softeners are widely used both in institutional laundries and also in domestic washing. It is assumed that these cationic quaternary ammonium compounds are readily absorbed onto the fabric substrate by virtue of their positive charge.

The most commonly used fabric softener of this type is distearyl dimethylammonium chloride (cf. S. Billenstein et al, J. Am. Oil Chem. Soc. 61 (1984), pp. 353 to 357). Although fabric softeners of this type show excellent softening properties, they are also attended by certain disadvantages. That is, the fabrics treated with them show reduced absorbency compared with untreated fabrics, which can be unpleasant to the user, for example in the case of articles of clothing worn in contact with the skin and in the case of terry towels. Fabric softeners of the afore-mentioned type often cannot be completely removed from the fabric during washing, so that, despite correct dosage, there is occasionally an accumulation of the softening agents which again results in reduced absorbency of the fabrics. Another serious disadvantage of such fabric softeners is their corrosive effect on metal surfaces caused by the chloride anion.

There has been no shortage of attempts to improve the properties of fabric softeners based on quaternary ammonium compounds. Thus, it is known from U.S. Pat. No. 3,636,114 that the absorbency of treated fabrics can be improved by using quaternary ammonium compounds containing two long-chain 2-hydroxyalkyl radicals. Quaternary ammonium compounds containing two long-chain 2-hydroxy-3-alkoxypropyl groups are known from U.S. Pat. Nos. 3,932,495; 3,972,855 and 4,104,175. German patent application No. 16 19 043 describes softeners which contain quaternary ammonium compounds having only one long alkyl radical and 3 short alkyl radicals, wherein the 3 short alkyl radicals may contain hydroxyl and ether groups. Dutch patent application No. 86/08958 and U.S. Pat. No. 3,591,405 describe quaternary ammonium compounds wherein the hydrophobic radicals are hydroxyalkyl groups or alkyl groups attached to the nitrogen by ethoxy groups. However, none of these attempted solutions was satisfactory either because the modified quaternary ammonium compounds are difficult to prepare and, accordingly, are unsuitable for practical application, or because the softening effect is too weak.

Accordingly, an object of the present invention is to provide new quaternary ammonium compounds which may readily be obtained from readily available starting materials. The new compounds are intended to leave the absorbency of the fabrics treated with them intact despite their favorable softening effect and to be completely removable during the washing of the fabrics. In addition, they are to have no corrosive effect on metal surfaces.

DESCRIPTION OF THE INVENTION

Other than in the operating examples, or where otherwise indicated, all numbers expressing quantities of ingredients or reaction conditions used herein are to be understood as modified in all instances by the term "about".

Accordingly, the present invention relates to quaternary 2-alkylimidazolinium salts corresponding to the following general formula

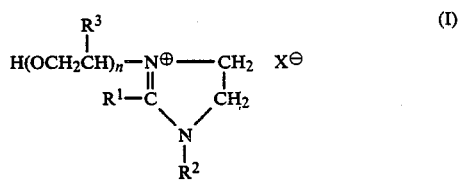

wherein $R^1$ represents a straight-chain or branched-chain substituted or unsubstituted alkyl or alkenyl radical containing from 7 to 21 carbon atoms, $R^2$ represents one of the following radicals

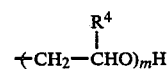

or

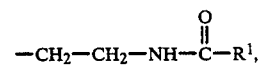

$R^3$ represents hydrogen or methyl, $R^4$ represents hydrogen or methyl, $X^-$ represents the anion of a non-oxidizing and non-corrosive inorganic acid or of an organic mono- or polycarboxylic acid, n statistically represents a whole or fraction number of from 1 to 20, and m represents an integer of from 1 to 3.

In addition, the invention relates to a process for the production of quaternary 2-alkyl-2-imidazolinium salts corresponding to the following general formula

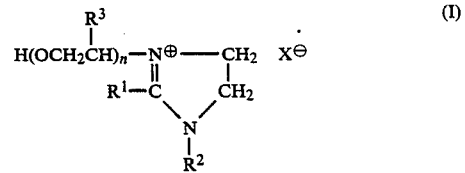

which is characterized in that imidazolines corresponding to the following general formula

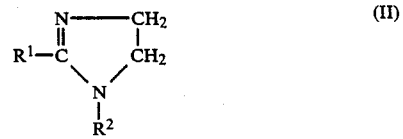

wherein $R^1$ and $R^2$ are as defined above for formula (I), are reacted in known manner with ethylene oxide or propylene oxide in the presence of 1 to 1.1 equivalents of an acid corresponding to the formula HX (III), in which X is as defined for formula (I), and optionally in the presence of water or of a mixture of water and a polar organic solvent and the products formed are optionally isolated and/or purified by methods known per se.

The present invention also relates to the use of quaternary 2-alkyl-2-imidazolinium salts corresponding to the following general formula

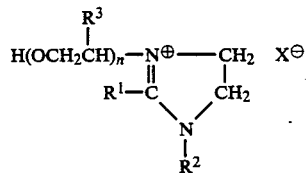

for softening fabrics.

In general formula (I) above, $R^1$ may represent a straight-chain or branched-chain, substituted or unsubstituted alkyl or alkenyl radical containing from 7 to 21 carbon atoms. Suitable alkyl radicals, therefore include, for example, the n-alkyl radicals from the group consisting of heptyl, octyl, nonyl, decyl, undecyl, dodecyl, tridecyl, tetradecyl, pentadecyl, hexadecyl, heptadecyl, octadecyl, nonadecyl, eicosyl or uneicosyl or single-branch or multiple-branch homologs thereof. In the imidazolinium salts of general formula (I) according to the invention, preferred substituents $R^1$ are those derived from fatty acids of natural origin, such as in particular straight-chain or branched-chain unsubstituted alkyl or alkenyl radicals containing from 7 to 17 carbon atoms from the above-mentioned group, straight-chain alkyl radicals containing from 7 to 17 carbon atoms being particularly preferred. Particularly advantageous in this respect are compounds corresponding to general formula (I), wherein $R^1$ represents an alkyl radical from the group consisting of n-heptyl, n-nonyl, n-undecyl, n-pentadecyl, n-heptadecyl, n-heptadec-8-enyl, n-heptadec-8,11-dienyl or mixtures thereof.

The quaternary 2-alkyl-2-imidazolinium salts of general formula (I) according to the invention also include compounds wherein $R^1$ represents a straight-chain or branched-chain alkyl radical containing from 7 to 17 carbon atoms which is substituted by one or more hydroxyl groups. Alkyl radicals $R^1$ of this type are those derived from parent fatty acids containing an OH-substituent. In this way, the solubility of the compounds in water shows a distinct improvement over compounds of general formula (I), wherein $R^1$ represents alkyl radicals, which are themselves readily soluble, the ready solubility of the compounds in water being essential for their optimal use.

In general formula (I) above, the substituent $R^2$ at the nitrogen atom in the 1-position of the 5-membered heterocyclic ring may represent one of the following two radicals:

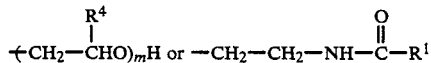

in these formulae, $R^4$ represents hydrogen or methyl, and m is an integer of from 1 to 3, so that suitable radicals include the hydroxyethyl radical, the 2-hydroxypropyl radical, the ethoxy-hydroxyethyl radical and the bis-(ethoxy)-hydroxyethyl radical of which the hydroxyethyl radical is particularly preferred.

In general formula (I) for quaternary 2-alkyl-2-imidazolinium salts according to the invention, X represents the anion of a non-oxidizing and non-corrosive inorganic acid or of an organic mono- or polycarboxylic acid. Examples of inorganic, non-oxidizing and non-corrosive acids, wherein the anion is represented by $X^\ominus$, include phosphorous acid, orthophosphoric acid, sulfuric acid and partial esters thereof, for example sulfuric acid monomethylester. However, $X^\ominus$ preferably represents the anion of an alkane carboxylic acid containing from 0 to 17 carbon atoms in the alkyl radical or of a monohydroxyalkane carboxylic acid containing from 1 to 17 carbon atoms in the alkyl radical, or the anion of an $\alpha,\omega$-dicarboxylic acid containing from 0 to 8 methylene groups, the methylene groups optionally carrying a hydroxy substituent, or the anion of fumaric, maleic or citric acid. Apart from the acids already specifically mentioned, the anion $X^\ominus$ may be derived, for example, from an alkane carboxylic acid from the group consisting of formic acid, acetic acid, propionic acid, butyric acid, valeric acid, caproic acid, oenanthic acid, caprylic acid, pelargonic acid, capric acid, undecanoic acid, lauric acid, myristic acid, palmitic acid, and stearic acid and isomers of these carboxylic acids, and from monohydroxyalkane carboxylic acids, such as glycolic acid, lactic acid, $\beta$-hydroxypropionic acid or 12-hydroxystearic acid.

However, $X^\ominus$ may also represent the anion of an $\alpha,\omega$-dicarboxylic acid from the group consisting of oxalic acid, malonic acid, succinic acid, glutaric acid, adipic acid, pimelic acid, suberic acid, azelaic acid, sebacic acid, nonane dicarboxylic acid or decane dicarboxylic acid. Other suitable anions $X^\ominus$ may be derived from $\alpha,\omega$-dicarboxylic acids belonging to the above-mentioned group, in which the methylene groups carry a hydroxy substituent. The anions of malic and tartaric acid are examples of anions from this group.

From the large group of the above-mentioned anions $X^\ominus$, the anions $X^\ominus$ of lactic acid and acetic acid are preferred in the compounds corresponding to general formula (I).

In general formula (I) above for quaternary 2-alkyl-2-imidazolinium salts according to the invention, the ammonium nitrogen atom in the 3-position of the heterocyclic, 5-membered ring carrier a substituent corresponding to the formula $-(CHR^3-CH_2-O)_nH$ wherein n represents a statistical value for the number of ethoxy groups which may lie continuously throughout the range of all whole or fraction numbers of from 1 to 20. The number of ethoxy or propoxy groups is determined by the quantity in which the olefin oxide employed for quaternization by the process according to the invention described in detail hereinafter is used in that process. As described in detail hereinafter, a uniform product containing a certain whole number n of alkoxy groups is only rarely formed in the process according to the invention, instead a whole range of differently alkoxylated compounds are formed alongside one another in the majority of cases.

Accordingly, $R^3$ in general formula (I) above may represent hydrogen or a methyl radical, depending on whether ethylene oxide or propylen oxide was used for quaterization.

In general formula (I) above, $R^3$ is preferably hydrogen.

The 2-alkylimidazolines of general formula (II) used in the production of the quaternary 2-alkylimidazolinium salts of general formula (I) according to the invention are known compounds which may be obtained by known methods of organic synthesis (cf. for example U.S. Pat. Nos. 4,058,488 and 4,212,983).

To prepare the imidazolines corresponding to general formula (II), fatty acid corresponding to the following general formula $$R^1—COOH \quad \text{(III)}$$

wherein $R^1$ is a straight-chain or branched-chain, substituted or unsubstituted alkyl or alkenyl radical containing from 7 to 21 carbon atoms, are best condensed with an aminoalkylamine derivative corresponding to the following general formula $$H_2N—CH_2—CH_2—NH—R^{2'} \quad \text{(IV)}$$

wherein $R^{2'}$ represents one of the following radicals $$\underset{|}{\overset{R^4}{CH_2—CH—OH}} \text{ or } CH_2—CH_2—NH_2$$

wherein $R^4$ is hydrogen or methyl.

Suitable fatty acids (III) include synthetic $C_8$–$C_{22}$ fatty acids or $C_8$–$C_{22}$ fatty acids obtainable from natural sources. Fatty acids of general formula (III), wherein $R^1$ is a straight-chain or branched-chain, unsubstituted alkyl or alkenyl radical containing from 7 to 17 carbon atoms, are preferably used for this reaction. On the other hand, it is also possible to use those fatty acids of general formula (III), wherein $R^1$ is a straight-chain or branched-chain $C_7$–$C_{17}$ alkyl radical substituted by one or more hydroxyl groups. Straight-chain fatty and hydroxyfatty acids are preferably used.

Examples of fatty acids which may advantageously be used for the production of the imidazolines corresponding to general formula (II) include caprylic acid, capric acid, lauric acid, myristic acid, palmitic acid, stearic acid, oleic acid, linolenic acid, ricinoleic acid, 12-hydroxy-stearic acid and 9,10-dihydroxystearic acid. The fatty acids mentioned may be used individually or in admixture for preparing the imidazolines (II). In general, fatty acid mixtures of the type accumulating in the cleavage of naturally occurring fats and oils are used for the preparation of the imidazolines (II). Individual fractions of these fatty acid mixtures may also be used for the synthesis of the imidazolines (II). Of particular significance in this regard are the mixtures of saturated and unsaturated fatty acids accumulating in the cleavage of coconut oil, which are frequently referred to as "cocosfatty acid", and the mixtures of saturated fatty acids obtained therefrom by hydrogenation of the double bonds present, which are also known as "hydrogenated cocosfatty acid".

Aminoethyl ethanolamine, aminoethyl propanolamine or diethylenetriamine may be used as a reactant corresponding to general formula (IV) above in the process according to the invention. The molar ratio of compound (III) to compound (IV), i.e. of fatty acid to aminoalkylamine derivative, may be in the range of from 1:1 to 2:1. Where a fatty acid is reacted with aminoethyl ethanolamine, the molar ratio between the reactants may be 1:1 whereas, where the fatty acid is reacted with diethylenetriamine, the molar ratio may be 2:1.

The condensation reaction may be carried out at a reaction temperature of from 150° to 240° C., and preferably at a reaction temperature of from 150° to 200° C. The water of reaction formed is continuously removed from the reaction mixture by simple or azeotropic distillation using a suitable solvent. In the reaction of fatty acid with aminoethyl ethanolamine, a solvent is generally used as entraining agent for the water formed during the reaction. The reaction of the fatty acid with diethylenetriamine may even be carried out in the absence of a solvent. The quantity of solvent used should be gauged in such as way that a final temperature of from 150° to 240° C. and preferably of from 150° to 200° C. may be reached for the reaction mixture as a whole. In this regard, toluene and xylene have proven to be particularly suitable solvents. Towards the end of the reaction, the pressure in the reaction zone is slowly reduced, preferably to a final pressure of from 10 to 20 mbar, to remove any solvent present and to drive out any water of reaction to be eliminated.

In another suitable process for the production of the imidazolines corresponding to general formula (II) esters of fatty acids corresponding to general formula (III) with short-chain alcohols, particularly fatty acid methylester or ethylester, are used as starting material. The observations made on the fatty acids in connection with the synthesis of the imidazolines described in the foregoing apply correspondingly to the fatty acid component of these esters. In this case, too, it is possible to use individual fatty acid esters or mixtures of fatty acid esters. It is preferred to use ester mixtures which may be derived on the one hand from the transesterification of natural fats and oils with short-chain alcohols or, on the other hand, from the esterification of cleavaged fatty acid mixtures with short-chain alcohols.

In this process, the first reaction step comprises aminolysis of the fatty acid esters, the short-chain alcohol of the ester being released and distilled off from the reaction mixture to displace the equilibrium. Aminolysis begins at a temperature as low as 60° C., while temperatures of from 150° to 240° C. are required for the subsequent ring-closing reaction accompanied by elimination of water, so that the overall reaction temperatures are in the range of from 60° to 240° C. To accelerate aminolysis, an alkaline catalyst, for example, sodium hydroxide, potassium hydroxide or sodium methylate, may be added to the mixture of starting materials. The reaction may be carried out in the absence of a solvent. However, it has proven to be best to carry out the second part of the synthesis in such a way that the water formed is distilled off from the reaction mixture in the form of an azeotrope with a suitable water-immiscible organic solvent, such as toluene or xylene. In the same way as for synthesis from the free fatty acids, the molar ratio of fatty acid ester to aminoalkylamine derivative may again be in the range of from 1:1 to 2:1.

Finally, the imidazolines corresponding to general formula (II) may also be directly prepared from fats and oils of natural origin which are known to be triglyceride mixtures of fatty acids corresponding to general formula (III). Suitable naturally occurring triglyceride mixtures include, for example, soya oil and tallow. Coconut oil is of particular importance in this regard. The basic conditions for this process are virtually the same as for the process just described, except that the glycerol released is generally not separated off, but remains in the reaction mixture. The molar ratio of fatty acid triglyceride to aminoalkylamine derivative may be in the range of from 1:3 to 2:3.

To carry out the process according to the invention for the preparation of the quaternary 2-alkyl-2-imidazolinium salts corresponding to general formula (I), from 1 to 1.1 equivalents of an acid HX (for HX, see the definition given in connection with the compounds of general formula (I)) is added to the imidazolines of general formula (II) per mole.

The addition of the acid may optionally be accompanied by an addition of water. Because of the instability of the imidazolines in alkaline medium, the water is added after the acid. It has been found to be particularly advantageous to add a mixture of water with an organic polar solvent rather than water alone to the reaction mixture. Preferred solvents of this type include $C_1$–$C_6$ alcohols, for example methanol, ethanol, propanol, n-butanol, n-hexanol or branched-chain isomers thereof. A mixture of water and i-propanol in a ratio by volume of 1:1 is particularly preferred.

Ethylene oxide or propylene oxide is then introduced into the mixture of imidazoline, acid, water and, optionally, solvent. The molar ratio of imidazoline to alkylene oxide is with particular advantage in the range of from 1:1 to 20:1. A preferred molar ratio for the reactants is from 1:3 to 1:10. Ethylene oxide is advantageously used as the alkylene oxide.

The reaction is carried out over a period of from 2 to 6 hours at a temperature of from 80° to 100° C. and under a slight excess pressure. The pressure is preferably in the range of from 1 to 5 bar. In order to arrest the increase in viscosity which normally occurs in the production of surfactants, water may optionally be added in this stage of the reaction to adjust the viscosity of the reaction mixture to a value of no higher than 10,000 mPas under the reaction conditions so that the mixture can still be pumped under the reaction conditions.

The quaternary 2-alkyl-2-imidazolinium salts corresponding to general formula (I) obtained in the reaction mixture may be isolated and purified by known methods. This may be done, for example, by distilling off the solvent and isolating or purifying the product obtained by crystallization, recrystallization, etc.

The compounds corresponding to general formula (I) are cationic surfactants which have a surprisingly good softening effect on cotton fabrics. The compounds corresponding to general formula (I) have the advantage over conventional softeners that the absorbency present in untreated fabrics is in no way affected by the softening treatment with the compounds corresponding to general formula (I). According to the invention, the compounds corresponding to general formula (I) are used for softening fabric, particularly cotton fabrics.

The invention is illustrated by the following examples.

EXAMPLE I

Alkoxylated 2-alkyl-2-imidazolinium salts corresponding to general formula (I) were produced as follows.

478.4 g (4.6 moles) of aminotheyl ethanolamine, 1.3 g of hyperphosphorous acid (50%) and 150 ml of xylene were initially introduced into a 2-liter glass apparatus equipped with a stirrer, water separator, thermometer and gas inlet pipe and mixed with 824.0 g (4.0 moles) of coconut oil fatty acid (general formula (II), wherein $R^1$ was a $C_8$–$C_{18}$ alkyl radical). The mixture was then heated under reflux to a sump temperature of 208° C. while nitrogen was introduced. After 165 g amine-containing water had separated, xylene and excess amine were distilled off up to a final pressure of 20 mbar and a sump temperature of 220° C.

1098 g of a pale yellow, oily liquid which solidified after a while were obtained.

| Analytical data: | |
| --- | --- |
| Nitrogen (total) | 10.1% |
| Nitrogen (basic) | 5.0% |
| Imidazoline (UV-spectrometric) | 98% |
| Diamide (exchanger flow) | 1.5% |

82.5 g of water and 60.0 g (0.6 mole) of a 90% lactic acid were introduced into a stirrer-equipped autoclave and mixed with 168.0 g (0.6 amine equivalent) of the imidazoline obtained as described above. The autoclave was closed and the air displaced by purging with nitrogen.

132.0 g (3.0 moles) of ethylene oxide were then introduced at 80° to 85° C. in such a way that the pressure did not exceed 3 bar. On completion of the addition, the mixture was left to react for 4 hours at 80° to 85° C.

440.2 g of a yellow, low-viscosity clear liquid were obtained having an acid number of 2.8. (The calculated acid number of the mixture before the reaction would be 76.1). This gives a conversion of 96.3% to the quaternary ammonium compound.

HPLC analysis produced an ethylene glycol content of 14.2% and 0.38% of diethylene glycol.

TABLE 1

| Compound No. | Parent fatty acid for A $R^1COOH$ | Alkylene oxide (moles) | Solvent (%) $H_2O$ | PG* | Acid number before reaction | Acid number after reaction | Conversion (%) from **T. Titr. | Acid No. | Consistency of the product |
| --- | --- | --- | --- | --- | --- | --- | --- | --- | --- |
| 1 | $C_8$–$C_{18}$ coconut oil fatty acid | 3 EO | 11.5 | 8.0 | 89.9 | 13.7 | 82.0 | 84.8 | homogeneous, low-viscosity liquid |
| 2 | lauric acid | " | 12.2 | 9.0 | 90.1 | 19.0 | 77.5 | 78.9 | 50%, very low viscosity |
| 3 | $C_8$–$C_{18}$ coconut oil fatty acid | " | 20 | — | 89.4 | 15.1 | — | 83.1 | 40%, very low viscosity |
| 4 | " | 5 EO | 20 | — | 96.3 | 2.8 | — | 96.3 | 50%, very low viscosity |
| 5 | " | 3 PO | 20 | — | 82.5 | 17.99 | — | 78.3 | homogeneous, low-viscosity liquid |

*1,2-propylene glycol
**Two-phase titration

Alkoxylated imidazolinium salts corresponding to general formula (I) were similarly prepared from other basic fatty acids. The results are shown in Table 1 above.

EXAMPLE II

Other compounds of general formula (I) according to the invention were produced as follows.

2189.6 g (8.0 moles) of a technical oleic acid and 2.5 g of hyperphosphorous acid (50%) were introduced into a 4-liter glass flask equipped with a stirrer, descending Liebig condenser, thermometer and gas inlet pipe. 412 g (4.0 moles) of diethylenetriamine were added to the reaction mixture at 65° C. while nitrogen was introduced. During the following three-hour period of heating to 200° C. with introduction of nitrogen, a vigorous elimination of water began at 148° C. After a residence time of 1 hour at 200° C., a total of 154 g of distillate had collected. The reaction zone was then gradually evacuated to a final pressure of 20 mbar, more distillate being collected. The reaction mixture was then stirred for 1 hour at 210° to 220° C. while the vacuum was maintained.

2380 g of a yellow, medium-viscosity liquid were obtained.

| Analytical data: | |
|---|---|
| Nitrogen (total) | 7.0% |
| Nitrogen (basic) | 2.35% |
| Imidazoline (UV-spectrometric) | 99.0% |

The imidazoline was ethoxylated in the same way as described in Example I. For this purpose, 66.0 g of water, 30.0 g (0.3 mole) of lactic acid (90%), 182.6 g (0.3 amine equivalent) of imidazoline and 66.0 g (1.5 moles) of ethylene oxide were initially introduced into the reaction vessel.

342 g of a jelly-like paste having an acid number of 4.5 were obtained in the same way as described in Example I. (The calculated acid number of 98.8). This gives a conversion of 90.8% to the alkoxylated 2-alkyl-2-imidazolinium compound corresponding to general formula (I). HPLC analysis of the product provided an ethylene glycol content of 14.3% and 0.38% diethylene glycol.

Further compounds corresponding to general formula (I) were obtained by the method described above. The results are shown in Table 2 below.

EXAMPLE III

This example gives the results of performance tests with the compounds of this invention.

(a) Softening effect

The softening effect of the compounds corresponding to general formula (I) was tested on cotton terry fabrics which had been made hard by repeated washing. The fabric samples were gently moved for 3 minutes in an aqueous liquor (tapwater 20° German hardness; liquor ratio 1:20) which contained 0.5% by weight active substance, based on the weight of the fabrics. The fabrics were then substantially freed from adhering treatment liquor by squeezing and were dried in air. The softness of the dried fabrics was assessed by feel by a group of people experienced in tests of this type.

(b) Rewettability

Rewettability was tested on 2×2 cm pieces of cotton fabrics which had been pretreated as described above. The dry fabric samples were placed on the surface of tapwater at room temperature. The period of time after which the samples were completely wetted and sank was measured with a stopwatch.

The tests were carried out with compounds 6, 8, 10, 11, 12 and 15 according to the invention. (see Table 2). Distearyl dimethylammonium chloride (A), a commercial softener, was included in the test for comparison purposes.

The results obtained are shown in Table 3 below in which the compounds tested are listed in such a way that their softening effect increased in the ascending direction.

TABLE 3

| Softening effect and rewettability | | |
|---|---|---|
| Compound | Softening effect | Completely wetted after (seconds) |
| A* | Very good | considerably longer than 300 |
| 15 | ↑ | 2.5 |
| 11 | ↑ | 2.5 |
| 13 | ↑ | 1.0 |
| 6 | ↑ | 2.5 |
| 10 | ↑ | 1.5 |
| 8 | ↑ | 2.0 |
| 12 | good | 1.5 |

*Comparison softener

TABLE 2

| Compound No. | Parent fatty acid for B $R^1COOH$ | Alkylene oxide (moles) | Solvent (%) $H_2O$ | PG* | Acid number before reaction | Acid number after reaction | Conversion (%) from **T. Titr. | Acid No. | Consistency of the product |
|---|---|---|---|---|---|---|---|---|---|
| 6 | oleic acid product dist. | 3 EO | 7.9 | 12.1 | 54.0 | 6.4 | 82 | 88.0 | opaque, fluid paste |
| 7 | 75 pbw. oleic acid 25 pbw. stearic acid | " | 7.9 | 12.1 | 54.0 | 7.8 | — | 85.6 | tallow-like paste |
| 8 | oleic acid | " | 20 | — | 54.0 | 14.3 | — | 73.5 | gell-like paste |
| 9 | " | 5 EO | 20 | — | 48.8 | 4.5 | — | 90.8 | " |
| 10 | " | 2 EO | 20 | — | 57.0 | 32.5 | — | 43.0 | " |
| 11 | $C_8$–$C_{10}$ and $C_{16}$–$C_{18}$ fatty acids, molar ratio 1:1 | 3 EO | 20 | — | 64.4 | 11.6 | — | 82.0 | salve-like paste |
| 12 | oleic acid | 3 PO | 20 | — | 51.4 | 9.8 | — | 80.9 | liquid, ready separation |
| 13 | " | 5 PO | 20 | — | 45.4 | 1.3 | — | 97.1 | homogeneous, low-viscosity liquid |
| 14 | 75 pbw. oleic acid 25 pbw. stearic acid | 5 PO | 20 | — | 45.4 | 1.2 | — | 97.3 | lard-like paste |
| 15 | stearic acid | 3 PO | 20 | — | 51.4 | 7.1 | — | 86.2 | tallow-like paste |

*1,2-propylene glycol
**Two-phase titration (c) Compatibility with anionic surfactants To test compatibility with anionic surfactants, compounds 1 to 5 (see Table 1) were each mixed with sodium alkylether sulfate based on an adduct of 2 moles of ethylene oxide with a mixture of $C_{12}$ and $C_{14}$ fatty alcohol (ratio by weight 70:30) in a molar ratio of anionic surfactant to cationic surfactant of 3:1 and aqueous solutions having a total surfactant content of 10% by weight were prepared from the mixtures obtained. Cetyl trimethylammonium chloride (B) was included in the test for comparison purposes. The results obtained are shown in Table 4 below (+ =compatible; — =incompatible).

TABLE 4

| Compatibility with anionic surfactants | |
|---|---|
| Compound | Compatibility |
| 1 | + |
| 2 | + |
| 3 | + |
| 4 | + |
| 5 | + |
| B | +- (cloudy) |

The results are summarized as follows.

The 2-alkyl-2-imidazolinium salts of general formula (I) according to the invention are virtually equivalent to the commercial distearyl dimethylammonium chloride (A) in their softening effect. However, it was surprisingly found that the fabrics treated with the compounds of formula (I) according to the invention show excellent rewettability which is almost completely absent from the fabrics treated with the conventional softener. It can also be seen from Table 3 that the softening effect of the new compounds can be regulated through their nature and degree of alkoxylation. In addition, the compounds according to the invention show very high compatibility with anionic surfactants (Table 4).

We claim:

1. A quaternary 2-alkyl-2-imidazolinium salt corresponding to the formula

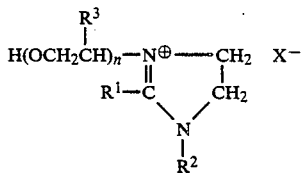

(I)

wherein
R$^1$ represents a straight-chain or branched-chain substituted or unsubstituted alkyl or alkenyl radical containing from 7 to 21 carbon atoms,
R$^2$ represents the following radical

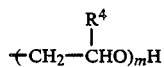

R$^3$ represents hydrogen or methyl,
R$^4$ represents hydrogen or methyl,
X$^\ominus$ represents the anion of an inorganic acid selected from phosphorous acid, orthophosphoric acid, sulfuric acid, and partial esters thereof, or the anion of an organic mono- or polycarboxylic acid, n statistically represents a whole or fraction number of from 1 to 20, and
m represents an integer of from 1 to 3.

2. A salt in accordance with claim 1, wherein R$^1$ represents a straight-chain or branched-chain, unsubstituted alkyl or alkenyl radical containing from 7 to 17 carbon atoms.

3. A salt in accordance with claim 1 wherein R$^1$ represents an alkyl radical selected from the group consisting of n-heptyl, n-nonyl, n-undecyl, n-tridecyl, n-pentadecyl, n-heptadecyl, n-heptadec-8-enyl, n-heptadec-8,11-dienyl or a mixture thereof.

4. A salt in accordance with claim 1 wherein R$^1$ represents a straight-chain or branched-chain $C_7$-$C_{17}$ alkyl radical substituted by one or more hydroxyl groups.

5. A salt in accordance with claim 1 wherein R$^2$ represents a hydroxyethyl radical.

6. A salt in accordance with claim 1 wherein X$^\ominus$ represents the anion of an alkane carboxylic acid containing from 0 to 17 carbon atoms in the alkyl radical or of a monohydroxyalkane carboxylic acid containing from 1 to 17 carbon atoms in the alkyl radical, or the anion of an α,ω-dicarboxylic acid containing from 0 to 8 methylene groups wherein the methylene groups may carry a dihydroxy substituent, or the anion of fumaric acid, maleic acid or citric acid.

7. A salt in accordance with claim 6 wherein the anion X$^\ominus$ is the anion of lactic acid or acetic acid.

8. A salt in accordance with claim 1 wherein n statistically represents a whole or fraction number of from 1 to 10.

9. A salt in accordance with claim 1 wherein R$^3$ represents hydrogen.

10. The process of softening a laundered fabric comprising contacting said laundered fabric with a quaternary 2-alkyl-2-imidazolinium salt corresponding to the formula

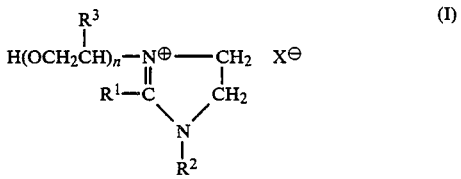

(I)

wherein
R$^1$ represents a straight-chain or branched-chain substituted or unsubstituted alkyl or alkenyl radical containing from 7 to 21 carbon atoms,
R$^2$ represents the following radical

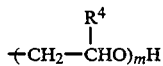

R$^3$ represents hydrogen or methyl,
R$^4$ represents hydrogen or methyl,
X$^\ominus$ represents the anion of an inorganic acid selected from phosphorous acid, orthophosphoric acid, sulfuric acid, and partial esters thereof, or of an organic mono- or polycarboxylic acid,
n statistically represents a whole or fraction number of from 1 to 20, and
m represents an integer of from 1 to 3.

* * * * *